(12) United States Patent
Ljung et al.

(10) Patent No.: US 6,328,934 B1
(45) Date of Patent: Dec. 11, 2001

(54) DEVICE FOR DETECTION OF WHEN A TEST PROBE GETS INTO CONTACT WITH A LIQUID SURFACE

(75) Inventors: Arne Ljung; Juhan Kivineeme, both of Uppsala (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/242,518

(22) PCT Filed: Sep. 15, 1997

(86) PCT No.: PCT/SE97/01547

§ 371 Date: Jan. 5, 2000

§ 102(e) Date: Jan. 5, 2000

(87) PCT Pub. No.: WO98/12513

PCT Pub. Date: Mar. 26, 1998

(30) Foreign Application Priority Data

Sep. 17, 1996 (SE) .................................................. 9603379

(51) Int. Cl.[7] ............................. G01F 23/24; G01F 23/26
(52) U.S. Cl. .............................. 422/119; 422/50; 422/62; 422/68.1; 422/82.01; 422/82.02; 422/100; 324/658; 324/679; 324/691; 324/705; 324/709; 324/722; 324/724
(58) Field of Search ........................ 422/50, 62, 68.1, 422/82.01, 82.02, 100, 119; 324/649, 658, 663, 664, 665, 667, 674, 679, 686, 689, 691, 693, 694, 705, 709, 722, 724

(56) References Cited

U.S. PATENT DOCUMENTS

| | | | |
|---|---|---|---|
| 4,010,650 | * 3/1977 | Piatkowski, Jr. | ..................... 73/304 C |
| 4,968,946 | * 11/1990 | Maier | ..................... 324/671 |
| 5,304,347 | 4/1994 | Mann et al. . | |
| 5,512,838 | * 4/1996 | Roach | ..................... 324/754 |

FOREIGN PATENT DOCUMENTS 0288215  10/1988  (EP) .
0338400  10/1989  (EP) .

* cited by examiner

*Primary Examiner*—John Kim
(74) *Attorney, Agent, or Firm*—Dinsmore & Shohl LLP

(57) ABSTRACT

A device for detection of when at test probe of conducting material contacts a liquid surface includes a test probe of conducting material. The test probe is electrically screened by an insulated screen, with a part of the test probe projecting in front of the screen. The test probe is connected to a first alternating voltage source via a first impedance and to one input of a differential amplifier, and the screen is connected to a second alternating voltage source via a second impedance and to another input of the differential amplifier. An output of the differential amplifier is connected to one input of a first multiplicator and to one input of a second multiplicator, and another input of the first multiplicator is connected to a third alternating voltage source, and another input of the second multiplicator is connected to a fourth alternating voltage source. An output voltage of the fourth voltage source is phase shifted relative to an output voltage of the third alternating voltage source and a signal processing unit is connected to the outputs of the first and second multiplicators and is capable of, based on the output signals of the multiplicators, deriving a first signal representing the resistvie load of the test probe and a second signal representing the capacitive load if the test probe, and, when the resistive load is low and the capacitive load is high, providing a signal as an indication that the test probe has contacted a liquid surface.

15 Claims, 1 Drawing Sheet

DEVICE FOR DETECTION OF WHEN A TEST PROBE GETS INTO CONTACT WITH A LIQUID SURFACE

TECHNICAL FIELD

The present invention relates to a device for detection of when a test probe of conducting material gets into contact with a liquid surface.

PRIOR ART

During, for example, pipetting it is very important to rapidly and safely detect when the tip of the pipette gets into contact with the liquid surface. An erroneous detection may lead to that the pipetting is not performed and an absent or delayed detection may result in contamination of the tip of the pipette.

The level detection procedures used by tradition today are either conductive, capacitive, hygroscopic, optic or acoustic.

Conductive level detectors operates in such a way that the conductivity (ability to conduct) between two measuring points are compared with a pre-set value. If the conductivity is higher (or lower) than the pre-set value, this represents a signal that a liquid or, where appropriate, a septum is found. The conductive detection procedures are, however, impaired by the disadvantages that they demand two test probes, that there is a risk that moisture will shorten the test probes, that solutions with low ion concentration, e.g. distilled water, can not be detected, that there is a risk for electrolysis of the detected solution and that it is impossible to distinguish between whether the test probes have got into contact with a septum or the liquid, in the case this is covered by a septum.

Capacitive level detectors operate by capacitance changes. A freely suspended test probe, in the shape of a conductor, has a certain capacitance relative to the surrounding and this capacitance increases when such a test probe gets into contact with the liquid or, where appropriate, with a septum. The disadvantage with the capacitive detection procedures is that it is impossible to distinguish between whether the test probe has got into contact with a septum or the liquid, in the case this is covered by a septum.

Hygroscopic detection procedures operate with pressure variations during aspiration in progress. A slow aspiration is started, whereupon the pipette is lowered towards the liquid surface. When the tip of the pipette touches the liquid surface, or where appropriate, with a septum, a pressure wave appears in the tube system, which pressure wave is detected. The disadvantages with the hygroscopic detection procedures are that it is not possible to distinguish between whether the tip of the pipette has got into contact with a septum or the liquid, that the aspiration has to be performed during the detection, that considerable demands are put on tubes and tube arrangement and that such procedures are slow.

Optical level detectors search for the liquid surface by detecting reflected light. The disadvantages with optical detection procedures are that the detector is easily contaminated, the optical detectors can not distinguish between foam and liquid and that special, light conducting test probes are required.

Acoustical detectors operate in the same way as a sonar. Such detectors emit sound which bounces on the liquid surface or, where appropriate, a septum. The detector measures in this connection the time elapsing for the sound to travel from the detector, bounce on the liquid surface and travel back to the detector. If the measured time is less than a predetermined limit, this may be interpreted as an indication of that the liquid surface/septum is reached. The acoustic detection procedures have the disadvantages that they demand special, sound conducting test probes and that they are not able to distinguish between a septum and a liquid.

SUMMARY OF THE INVENTION

The aim of the present invention is therefore to provide a device, which do not present the above mentioned disadvantages, for detection of when a test probe gets into contact with a liquid surface, independent of whether this is covered by a septum or not.

This is achieved by the device according to the invention, by means of that the test probe is electrically screened by a screen, isolated from the test probe, with a part of the test probe projecting in front of the screen, that the test probe on one hand is connected to a first alternating voltage source via a first impedance and on the other to one of the inputs of a differential amplifier, while the screen on one hand is connected to a second alternating voltage source via a second impedance and on the other to the other input of the differential amplifier, that the output of the differential amplifier on one hand is connected to one of the inputs of a first multiplier, whose other input is connected to a third alternating voltage source, and on the other to one of the inputs of a second multiplicator, whose other input is connected to a fourth alternating voltage source, and that a signal processing unit is connected to the outputs of the multiplicators and disposed to based on the output signals o f the multiplicators derive on one hand a first signal, representing the resistive load of the test probe, and on the other a second signal, representing the capacitive load of the test probe, and to provide a signal when the resistive load is low contemporarily as the capacitive load is high as an indication of that the test probe has got into contact with the liquid surface.

DESCRIPTION OF THE DRAWINGS

The invention is described below in more detail with reference to the accompanying drawing, in which FIG. 1 schematically illustrates a block diagram for an embodiment of a device according to the invention

PREFERRED EMBODIMENTS

Although, the embodiment of the invention, described in the following, relates to detection of a liquid surface in connection with pipetting of the liquid by a pipette of conducting material, it is understood that the invention in no sense is limited to be applied solely to pipettes, but may be used in arbitrary connections, where a liquid surface is to be detected by means of a zest probe of a conducting material.

Figure 1:
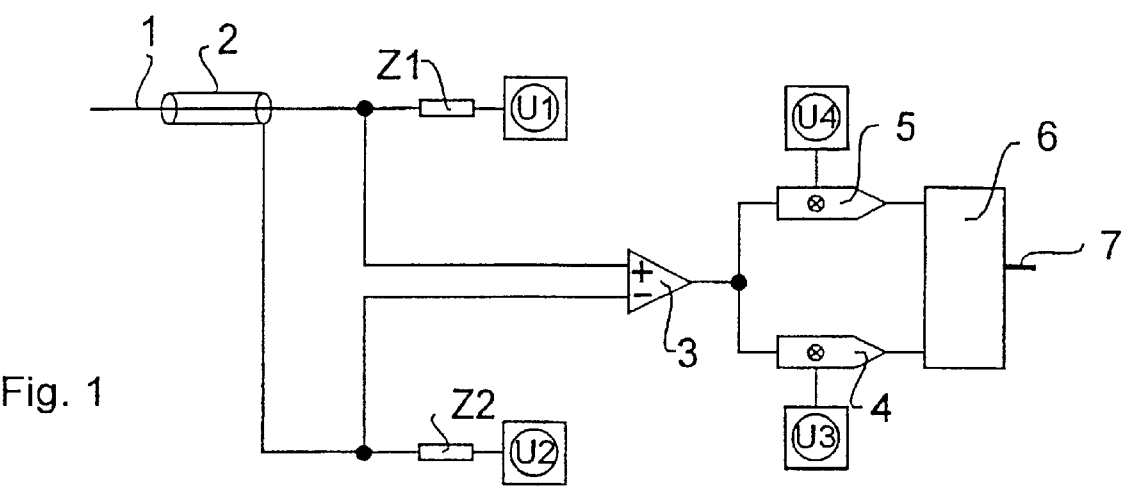

In the embodiment of a device according to the present invention, as shown in FIG. 1, is thus referring to a test probe in the form of a pipette of conducting material for pipetting of a not shown liquid. This liquid is assumed, in the shown embodiment, to be covered by a not shown septum. The pipette 1 is operated in a known per se by means of a not shown motor.

According to the invention, the pipette 1 is electrically screened by a screen 2, which extends around the pipette 1 and is electrically isolated from the same in a not further shown way. The screen 2 is disposed in such a way that the tip of the pipette 1 projects a distance in front of the screen 2.

The pipette 1 and the screen 2 are according to the invention connected to an alternating voltage source each, U1 and U2, respectively, via an impedance each, Z1 and Z2, respectively. The impedances Z1 and Z2 have different magnitudes. The alternating voltage sources U1 and U2 are disposed to give alternating voltages of the same frequency.

According to the invention, the pipette 1 and the screen 2 are also connected to one input each of a differential amplifier 3, which is disposed to detect alterations in the potential of the pipette 1 relative to the potential of the screen 2 depending on that the resistive and/or capacitive load of the tip of the pipette is changed when it is brought closer to the not shown liquid surface or, where appropriate, the not shown septum.

The output of the differential amplifier 3 is according to the invention connected to one of the inputs of two multiplicators 4 and 5, resp.

The other input of the multiplicator 4 is at the shown embodiment connected to a third alternating voltage source U3. The alternating voltage source U3 is disposed to generate an alternating voltage of the same frequency as for the alternating voltage sources U1 and U2.

The multiplicator 4 will generate an output signal over its output, which principally corresponds to a change in the resistive load of the tip of the pipette caused by an alteration of the potential of the pipette 1, but which to a certain extent also corresponds to an alteration of the potential of the pipette 1 caused by the capacitive load of the tip of the pipette.

The second input of the multiplicator 5 is connected to an alternating voltage source U4, which at the shown embodiment is disposed to generate a voltage which is phase shifted 90° relative to the voltage of the alternating voltage source U3. The multiplicator 5 will generate an output signal over its output, which principally corresponds to a change of the capacitive load of the tip of the pipette caused by an alteration of the potential of the pipette 1, but which to a certain extent also corresponds to an alteration of the potential of the pipette 1 caused by the resistive load of the tip of the pipette.

The phase shift between the voltages of the alternating voltage sources U3 and U4 does not have to be exactly 90°. In the general case, these both voltages should only be phase shifted relative to each other.

At the embodiment shown in FIG. 1, the output signals of the multiplicators 4 and 5 are fed, via a not shown low-pass filter each, to a signal processing unit 6, which is disposed to, based on the output signals of the multiplicators, decide when the tip of the pipette gets into contact with the not shown liquid surface independent of whether this is covered by a septum or not and in this connection generate an output signal over its output 7.

The signal processing unit 6 is disposed to, based on the output signals of the multiplicators, derive on one hand a first signal, corresponding to the resistive load of the pipette 1, and on the other a second signal, corresponding to the capacitive load of the pipette 1.

Based on these first and second signals, the signal processing unit 6 is further disposed to provide a signal over the output 7 when said First signal is low, which means that the pipette is not resistively loaded, as an indication of that the tip of the pipette 1 actually has got into contact with the liquid surface.

The signal processing unit 6 may of course fully or to a part be implemented by means of software.

At the shown embodiment, the pipette 1 may be connected to a not shown tube, which in turn is connected to a not shown dilutor.

According to the invention, in such cases also the tube to the dilutor is screened in a not shown manner by means of a tube screen, which is electrically connected to the screen of the pipette to prevent that the content in the tube, i.e. liquid and/or air, will influence the detection accuracy. With the purpose to increase the tolerance against different contents in the tube to the dilutor, the end of the tube screen is also connected with the inside of the tube in a not shown manner.

Figure 2A:
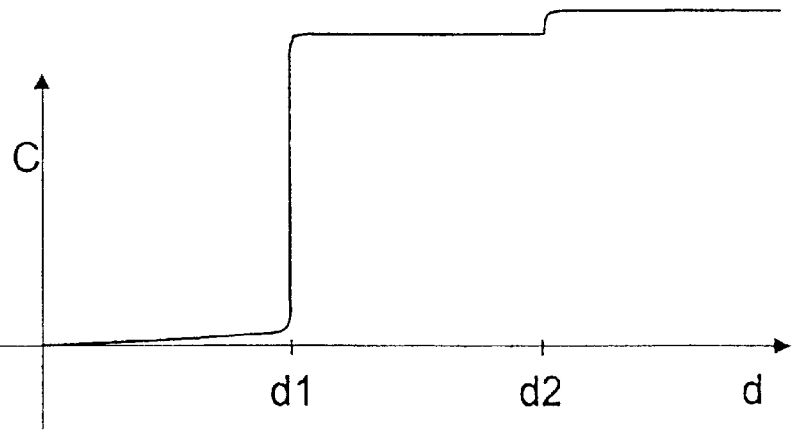
FIGS. 2a and 2b show different signal shapes, which appear in the embodiment of the device according to FIG. 1.
Figure 2B:
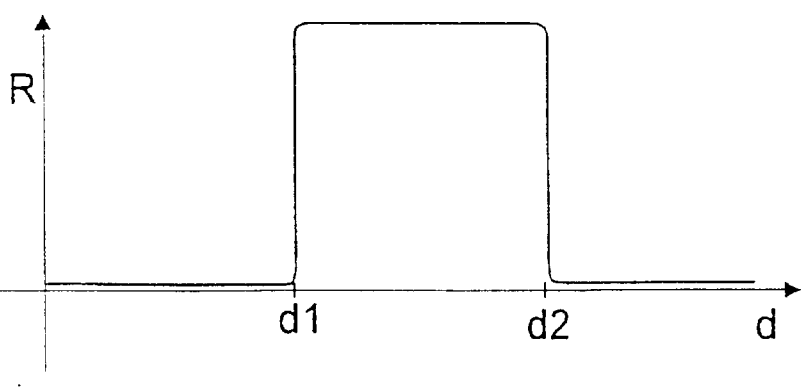

FIGS. 2a and 2b show examples of signals derived in the signal processing unit 6, according to FIG. 1, as a function of the movement distance d of the pipette 1, when the tip of the pipette 1 first gets into contact with a septum after moving a distance d1 and thereafter with a liquid surface after moving a distance d2.

FIG. 2a shows in this connection how the capacitive load C of the tip of the pipette is changed when the tip of the pipette gets into contact with the septum and thereafter with the liquid surface. When the tip of the pipette, after moving the distance d1, gets into contact with the septum, the capacitive load of the tip of the pipette rises very steeply.

As is clear from FIG. 2b, which shows the change of the resistive load R of the tip of the pipette, also this rises steeply contemporarily.

During the passage of the septum and as long as any part of the pipette tip touches the septum, i.e. when the pipette tip is moving from d1 to d2, the capacitive as well as the resistive load remains at a high level.

After passing the septum, the pipette tip gets into contact with the liquid surface. In this connection, the capacitive load increases somewhat, as is shown by FIG. 2a, while the resistive load of the pipette tip falls steeply to principally its value in air, as is shown by FIG. 2b.

The signal processing unit 6 is disposed to, based on the signals shown in FIGS. 2a and 2b, provide an output signal when the capacitive load, according to FIG. 2a, is high contemporarily as the resistive load, according to FIG. 2b, is principally zero, as an indication of that the pipette tip has got into contact with the liquid surface. How this should be implemented will probably be obvious for someone skilled in the art.

Accordingly, by means of the device according to the invention, a very accurate detection of when the pipette tip gets into contact with the liquid surface is achieved irrespective of whether this is covered by a septum or not.

What is claimed is:

1. A device for detecting when a test probe of conducting material contacts a liquid surface, comprising a test probe of conducting material, wherein the test probe is electrically screened by an insulated screen, with part of the test probe projecting in front of the screen, and further wherein:

the test probe is connected to a first alternating voltage source via a first impedance and to one input of a differential amplifier, and the screen is connected to a second alternating voltage source via a second impedance and to another input of the differential amplifier, an output of the differential amplifier is connected to one input of a first multiplicator and to one input of a second multiplicator, and another input of the first multiplicator is connected to a third alternating voltage source, and another input of the second multiplicator is connected to a fourth alternating voltage source, an output voltage of the fourth alternating voltage source is phase shifted relative to an output voltage of the third alternating voltage source; and a signal processing unit is connected to the outputs of the first and second multiplicators and is capable of, based on the output signals of the multiplicators, deriving a first signal representing the resistive load of the test probe and a second signal representing the capacitive load of the test probe, and, when the resistive load is low and the capacitive load is high, providing a signal as an indication that the test probe has contacted a liquid surface.

2. The device according to claim 1, wherein the output voltage of the fourth alternating voltage source is phase shifted 90° relative to the output voltage of the third alternating voltage source.

3. The device according to claim 2, wherein the first, second, third and fourth alternating voltage sources provide alternating voltages of the same frequency.

4. The device according to claim 3, wherein a low pass filter is connected respectively between each of the outputs of the first and second multiplicators and the signal processing unit.

5. The device according to claim 4, wherein the test probe comprises a pipette connected to a tube, the tube is electrically screened by a tube screen, and the tube screen is electrically connected to the insulated screen.

6. The device according to claim 5, wherein an end of the tube screen facing away from the pipette is electrically connected to the inside of the tube.

7. The device according to claim 2, wherein a low pass filter is connected respectively between each of the outputs of the first and second multiplicators and the signal processing unit.

8. The device according to claim 2, wherein the test probe comprises a pipette connected to a tube, the tube is electrically screened by a tube screen, and the tube screen is electrically connected to the insulated screen.

9. The device according to claim 1, wherein the first, second, third and fourth alternating voltage sources provide alternating voltages of the same frequency.

10. The device according to claim 9, wherein a low pass filter is connected respectively between each of the outputs of the first and second multiplicators and the signal processing unit.

11. The device according to claim 9, wherein the test probe comprises a pipette connected to a tube, the tube is electrically screened by a tube screen, and the tube screen is electrically connected to the insulated screen.

12. The device according to claim 1, wherein a low pass filter is connected respectively between each of the outputs of the first and second multiplicators and the signal processing unit.

13. The device according to claim 12, wherein the test probe comprises a pipette connected to a tube, the tube is electrically screened by a tube screen, and the tube screen is electrically connected to the insulated screen.

14. The device according to claim 1, wherein the test probe comprises a pipette connected to a tube, the tube is electrically screened by a tube screen, and the tube screen is electrically connected to the insulated screen.

15. The device according to claim 14, wherein an end of the tube screen facing away from the pipette is electrically connected to the inside of the tube.

* * * * *